United States Patent [19]

Hsu

[11] Patent Number: 4,827,023

[45] Date of Patent: May 2, 1989

[54] PROCESS FOR THE SELECTIVE FORMATION OF DIALKYL SUCCINATES

[75] Inventor: Chao-Yang Hsu, Media, Pa.

[73] Assignee: Sun Refining and Marketing Company, Philadelphia, Pa.

[21] Appl. No.: 126,321

[22] Filed: Nov. 27, 1987

[51] Int. Cl.[4] .............................................. C07C 67/38
[52] U.S. Cl. .................................. 560/204; 502/171; 502/230; 502/313; 502/326; 502/331; 560/190
[58] Field of Search ................ 560/204, 190; 502/171, 502/230, 313, 326, 331

[56] References Cited

U.S. PATENT DOCUMENTS

| | | | |
|---|---|---|---|
| 3,397,225 | 8/1968 | Fenton | 560/204 |
| 3,397,226 | 8/1968 | Fenton | 560/204 X |
| 3,530,168 | 9/1970 | Biale | 560/204 |
| 3,960,934 | 6/1976 | Gaenzler et al. | 560/204 X |
| 4,039,572 | 8/1977 | Funakoshi et al. | 560/204 X |
| 4,429,147 | 1/1984 | Agnes et al. | 560/97 X |
| 4,539,424 | 9/1985 | Jenck | 560/204 |
| 4,645,855 | 2/1987 | Reuvers et al. | 560/204 |
| 4,739,107 | 4/1988 | Drent | 560/204 |

OTHER PUBLICATIONS

Fenton et al., *Chemtech*, pp. 220–225, Apr. 1972.
James et al., *Journal of the American Chemical Society*, 98:7, pp. 1810–1823, Mar. 1976.
Stille et al., *J. Org. Chem.*, vol. 44, No. 20, pp. 3474–3482, 1979.

*Primary Examiner*—Werren B. Lone
*Assistant Examiner*—Vera C. Clarke
*Attorney, Agent, or Firm*—J. Edward Hess; Donald R. Johnson

[57] ABSTRACT

The invention discloses an improvement to the selective production of dialkyl succinates by the known process of oxidative carbonylation of an olefin with carbon monoxide, oxygen, and an alkyl alochol in the presence of a catalyst wherein the improvement comprises using a sulfone as the reaction solvent. The use of a sulfone, of which sulfolane is a preferred example, results in fast reaction rates and high selectivity to dialkyl succinates even in the absence of a dehydrating agent.

23 Claims, No Drawings

PROCESS FOR THE SELECTIVE FORMATION OF DIALKYL SUCCINATES

BACKGROUND OF THE INVENTION

It is known that various saturated and unsaturated esters of carboxylic acids such as acrylates, succinates, and $\beta$-alkoxycarboxylates can be derived simultaneously from olefins directly via oxidative carbonylation [U.S. Pat. Nos. 3,397,225 (1968), 3,397,226 (1968); Chemtech, 220–225 (1972)]. The oxidative carbonylation involves the reaction of an olefin with carbon monoxide, oxygen, and an alcohol (serving as an reactant and as a solvent) using a platinum group metal in a high oxidation state as a catalyst. [Equations (1) to (3) below].

(1)

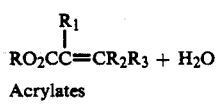

Acrylates

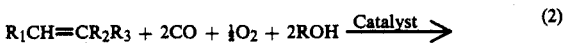

(2)

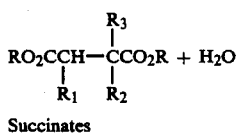

Succinates

(3)

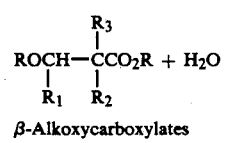

$\beta$-Alkoxycarboxylates where $R_1CH=CR_2R_3$ is the olefin defined below as structure (I) and ROH is an alkyl alcohol containing from 1–6 carbon atoms.

The catalyst used in the oxidative carbonylation preferably consists of a redox catalyst system comprising a catalytically active species of palladium and an oxidant.

Several drawbacks are encountered in this conventional oxidative carbonylation where succinates are the desired product: (1) The simultaneous formation of the competing esters shown in equations (1) and (3) above, and the production of by-products such as carbonates, oxalates, ketones, aldehydes, acetals, $CO_2$, and reductive carbonylation-derived saturated esters result in low succinate yield and increases the burdensome operations of product separation and purification; (2) The dehydrating agents often employed to favor ester production by removing the water of reaction are either expensive, non-regenerable organic compounds or regenerable inorganic agents with their own technological and operational difficulties; and (3) Gaseous mixtures of CO and $O_2$ have the inherent risk of explosion over a broad range of component ratios. Owing to these disadvantages, the oxidative carbonylation is impractical economically, especially for industrial applications.

Several attempts have been made recently to improve the practicability of oxidative carbonylation: U.S. Pat. No. 3,530,168 (1970) discloses that the addition of a biphyllic ligand such as triphenyl phosphine eliminates the requirement for a dehydrating agent and minimizes the formation of $CO_2$ and carbonates. However, the formation of esters is non-selective and undesirable quantities of reductive carbonylation by-products are obtained. According to U.S. Pat. No. 3,960,934 (1976), the use of a vanadium, chromium, iron, cobalt, nickel or copper compound in combination with a halide and a phosphine or a phosphite as a catalyst can avoid the formation of aldehydes or ketones as reaction by-products, but the yields and selectivities to dialkyl succinates are too low to be practical. U.S. Pat. No. 4,039,572 (1977) discloses the use of supported palladium catalysts to obtain high selectivity to dialkyl succinates but the total yields are too low to be industrially practical. Stille, et al, [J. Amer. Chem. Soc., 98, 1810 (1976), J. Org. Chem., 44, 3474 (1979)] and U.S. Pat. No. 4,429,147 (1980) disclose that dialkyl succinates can be produced selectively and in relatively high yields, but the reaction rates are slow and the reactions require the presence of large excess amounts of copper (II) salts as the oxidant.

It is therefore, an objective of this invention to provide an effective process for selective oxidative carbonylation of olefins to corresponding dialkyl succinates to afford both faster reaction rates and higher selectivity to the desired product. In one embodiment of this invention these beneficial results are achieved without using any dehydrating agent. An additional embodiment of this invention allows for simplified product separations and catalyst recycling operations. Another embodiment utilizes operating conditions and charge gas compositions which can prevent or minimize explosive conditions in the reaction system.

SUMMARY OF THE INVENTION

The present invention discloses the novel use of a sulfone solvent in the oxidative carbonylation of an olefin to increase the selective production of dialkyl succinates while maintaining a fast reaction rate. The olefin is reacted in a known manner with carbon monoxide, oxygen and an alkyl alcohol in the presence of a catalyst in a high oxidation state chosen from the platinum group metals, preferably palladium. The reaction is operable over a broad range of operating temperatures and pressures, depending on the relative economics of reactor and reactant costs for the dialkyl succinate production desired.

The use of the sulfone solvent increases the selectivity of the reaction to the desired dialkyl succinate product and reduces the formation of undesirable by-products such as alkyl carbonates which are formed when the alcohol reactant is present in great excess over the desired stoichiometric amount so that it may act as the solvent. The fast reaction rate and high selectivity to dialkyl succinates are possible in the sulfone solvent without the use of dehydrating agents, although such an agent may optionally be added to the reaction step of this invention.

DETAILED DESCRIPTION OF THE INVENTION

The present invention relates to a process for the selective production of dialkyl succinates from corresponding olefins employing oxidative carbonylation. More specifically, the oxidative carbonylation is performed by reacting an olefin with carbon monoxide, oxygen, and an alkyl alcohol in the presence of a catalyst and using a sulfone solvent. A unique feature of this invention is the use of a sulfone as the reaction solvent. Several advantages are gained in the sulfone solvent system: (1) Faster reaction rates and higher selectivities to dialkyl succinates are obtained without the use of a dehydrating agent, although such an agent may be employed in an additional embodiment of the invention for further operational advantages; (2) In another embodiment of the invention, the process may be carried out using only stoichiometric amounts of an alcohol as a reactant to greatly reduce the formation of the alcohol derived by-products, e.g., carbonates, oxalates, acetals, and formates which result when an excess of alcohol is used to provide the solvent medium; (3) Product separations and catalyst recycling may be facilitated, especially when sulfones with higher boiling points than the dialkyl succinate products are used, since the unreacted alcohol and the succinates can be distilled off and the catalyst remaining in the sulfone solvent can be easily recycled employing a conventional pump.

Olefins comprising 2-14 carbon atoms are suitable for this process and can be represented by structure (I) as shown below:

(I) $R_1CH=CR_2R_3$ wherein $R_1$ and $R_2$=H, alkyl, alkoxy, cyclic (aryl or aliphatic) hydrocarbon, substituted alkyl or substituted cyclic hydrocarbon group, $R_3$=H or methyl, and $R_1$, $R_2$ and $R_3$ may be the same or different. Examples of suitable olefins include ethylene, propylene, styrene, α-methyl styrene, stilbene, 1-butene, 2-butene, p-chlorostyrene, m-nitrostyrene, isobutylene, etc. of which ethylene, propylene, styrene, α-methyl styrene and isobutylene are preferred examples.

The alkyl alcohol used in the present invention include aliphatic alcohols having from one to six carbon atoms, such as methanol, ethanol, 1-propanol, 2-propanol, 1-butanol, 2-butanol, t-butanol, n-pentanol, n-hexanol and the like, preferably methanol, ethanol and the propanols.

Carbon monoxide and oxygen for this process can be introduced either as pure components or together with nitrogen, argon, and other inert gases as diluents. Air can be used as the oxygen source. Carbon monoxide together with air with the composition containing less than about 12% by volume of carbon monoxide can also be used to remain below the explosive limit of the mixture. The carbon monoxide and air can be charged into the reactor through a separated gas inlet system to prevent explosive mixtures in the charge stream, and preferably the gases are charged into the bottom of a reactor covered with a sulfone solvent which is non-flammable at the reaction conditions. The partial pressure of carbon monoxide and oxygen in the gas charging system can be carefully controlled so that an explosive gas mixture cannot form in the reactor system. It is desirable to introduce the gaseous reactants in proportions which will increase reaction rates and selectivity to dialkyl succinates. The preferable molar ratios are:

CO/olefin=2/1-10/1

$CO/O_2$=4/1-20/1 while operable ratios can vary from 1/1 to 50/1 for both of these ratios.

The catalyst utilized is a platinum group metal in a high oxidation state. The platinum group metal can be of the platinum sub-group, i.e., platinum, rhodium or ruthenium or of the palladium sub-group, i.e., palladium, uranium or osmium. Palladium is preferred because of its demonstrated greater activity. A more preferred catalyst is a catalyst system comprising a palladium metal or salt and an oxidant. The preferred palladium metals include finely divided palladium particles dispersed on supports such as alumina, silicate, and active carbon. Preferred palladium salts include palladium (II) halides, palladium (II) nitrate, palladium (II) nitrite, palladium (II) acetate, and palladium (II) acetylacetonate.

The oxidant is preferably a salt or other compound derived from multivalent metals which have higher oxidation potential than that required for oxidizing palladium metal to a palladium (II) state. Thus, the presence of an oxidant can prevent the formation of catalytically inactive palladium metal during the course of reaction. The metal salts are preferably from the group comprising copper, iron, manganese, chromium, molybdenum and vanadium metal salts. These salts or other compounds of the multivalent metals include halides, nitrates, nitriles, carboxylates, etc. of which cuprous halide is a preferred salt. Other organic oxidants such as quinones and alkyl nitrites can also be employed, preferably anthraquinone or benzoquinone or a nitrite containing the same alkyl group as the alcohol employed in the reaction. The oxidant can be applied in any desirable amount. However, the concentration of the oxidant used in the reaction is preferably restricted to catalytic amounts relative to the olefin reactants used.

In order to obtain high reaction rates and high selectivities to dialkyl succinates, it is essential to this invetion to use a sulfone as the solvent. The general formula of sulfones which are applicable for this purpose are shown as structures (II) to (IV):

(I)

(II)

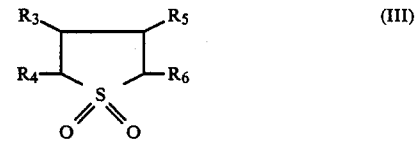

(III)

wherein $R_1$, $R_2$, $R_3$, $R_4$, $R_5$ and $R_6$ are alkyl or cyclic hydrocarbon groups which may be the same or different, and n≧4. The preferable sulfones are the ones having higher boiling points than that of the dialkyl succinate reaction products, i.e., above about 200° C. and, more preferably, the ones which are also liquid under room conditions, i.e., a melting point of greater than about 25° C. Examples of preferred sulfones are: sulfolane (tetramethylene sulfone), 2,4-dimethylsulfolane, 3-methylsulfolane and dimethyl sulfone. Sulfolane is a readily available commercial product sold by Aldrich Chemical Company and Kodak Chemical Company.

The oxidative carbonylation can be conducted over a broad range of relatively mild conditions, e.g., temperature range of from 25° C. to about 250° C., preferably from 50° C. to 150° C., and pressure range from atmospheric to about 2500 psig, preferably from 150 psig to 1400 psig.

The advantages of this invention are realized over a broad range of operating ratios between reactants, reactants and catalyst, and catalyst system components which are adjusted by those skilled in the art to balance the economics of various reactant and catalyst costs with the yields and selectivities of dialkyl succinates resulting from such changes. For example, molar ratios of olefin/palladium may range from 10/1 to 10,000/1, preferably from 50/1 to 1000/1 and molar ratios of oxidant/palladium (where an oxidant system as described above is employed) may range from 1/1 to 50/1, and preferably from 5/1 to 20/1.

Alcohol/olefin molar ratios may vary from 1/1 to 20/1, preferably 1/1 to 10/1. In one embodiment, this ratio may be limited to the theoretical stoichiometric ratio shown earlier in equation (2) to be 2/1. Ratios higher than 2/1, up to 20/1 and more preferably up to 10/1, may be utilized where the alcohol is also utilized as a co-solvent for the sulfone.

The total amount of solvent per mmol of palladium may range from 20 to 2500 ml, and preferably from 40 to 1000 ml.

Reaction time is measured as hourly space velocity (HSV), defined as the volume of feed gases charged per volume of liquid reactants charged (solvent, alcohol and catalyst system) per hour. HSV may range from 50–500 $hr^{-1}$, preferably 150–250 $hr^{-1}$ and most preferably about 195 $hr^{-1}$ depending on the economic balance of yield, selectivity and capital cost of the reactor and auxiliaries.

EXAMPLE 1

This example illustrates the oxidative carbonylation of ethylene in the presence of a sulfone solvent of the present invention.

A 300 ml Hastelloy ®-C autoclave reactor equipped with a magnetic drive stirrer, a gas inlet and outlet system, and a water cooled condenser was used for this invention so that a non-explosive gas mixture was continuously introduced into the reactor and the unreacted gaseous materials were vented continuously. A water cooled condenser was used to keep the liquid materials from flushing out of the reactor by the venting gases.

Palladium (II) chloride (0.444 g, 2.5 mmoles), copper (I) chloride (2.457 g, 25.0 mmoles), methanol (50 ml), and sulfolane (100 ml) were charged into the reactor. After the reactor was sealed, a constant flow of gaseous mixture consisting of air (flow rate=135 ml/minute), CO (200 ml/minute), ethylene (100 ml/minute), and $N_2$ (49 ml/minute) was continuously flowed into the reactor through the bottom of the liquid. The total gas pressure was adjusted to 500 psig using a back pressure regulator. After the reactor was heated to 100° C. for 2.0 hours while maintaining the same gas flow and pressure, the reactor was cooled and the liquid contents were analyzed using vapor phase chromatography. The following reaction product composition was obtained: dimethyl succinate (279.5 mmoles), methyl formate (4.3 mmoles), 1,1-dimethoxyethane (1.1 mmoles), dimethyl carbonate (2.0 mmoles), and methyl acrylate (2.0 mmoles). Other reaction products were negligable. The corresponding selectivity to dimethyl succinate (moles of dimethyl succinate divided by total moles of reaction products) was 97%.

EXAMPLE 2

This example illustrates the oxidative carbonylation of ethylene using the same procedure as described in Example 1 but no sulfone is used as the solvent.

The procedure of Example 1 was repeated with the use of methanol (150 ml) in lieu of the mixture of methanol (50 ml) and sulfolane (100 ml) used in Example 1. The liquid reaction products were analyzed to obtain: dimethyl succinate (211. mmoles), methyl formate (5.9 mmoles), 1,1-dimethoxyethane (25.0 mmoles), dimethyl carbonate (17.3 mmoles), and methyl acrylate (2.5 mmoles). The corresponding selectivity to dimethyl succinate was 81%.

EXAMPLE 3

This example illustrates the oxidative carbonylation of ethylene using a batch process similar to that disclosed in U.S. Pat. No. 3,397,226. This example, like example 2, is a prior art process and is included to show that other prior art processes are inferior to the present invention.

Palladium (II) chloride (0.555 g, 2.5 mmoles), copper (II) chloride (3.361 g, 25.0 mmoles), lithium chloride (0.530 g, 12.5 mmoles), and methanol (122 ml) were charged into a 300-ml Hastelloy ®-C autoclave reactor. After the reactor was sealed and purged with CO, ethylene (14.5 g, 517.3 mmoles) was charged and then carbon monoxide was introduced into the reactor to increase the pressure to 600 psig. The reactor was quickly heated to 100° C., and more carbon monoxide was added to increase the total pressure to 950 psig, and then oxygen was added to make up the total pressure to 1000 psig. In a short period (2 to 3 minutes), the reaction pressure dropped to about 800 psi, whereupon carbon monoxide was added again to increase the reaction pressure to 950 psi, and then oxygen was also added again to make up the total pressure to 1000 psig. The above procedure was repeated several times until no further pressure drop was observed. After 4.0 hours of reaction at 100° C., the reactor was quickly cooled, and depressured. The liquid reaction products were analyzed as in the other examples to obtain: dimethyl succinate (385.3 mmoles), methyl formate (60.8 mmoles), 1,1-dimethoxyethane (60.5 mmoles), dimethyl oxalate (8.3 mmoles), methyl carbonate (7.7 mmoles) and methyl acrylate (14.5 mmoles). This corresponds to a selectivity of 72% to dimethyl succinate.

I claim:

1. In the process for the oxidative carbonylation of an olefin with carbon monoxide, oxygen and an alcohol in the presence of a platinum group metal catalyst to a dialkyl succinate, the improvement which comprises carrying out the oxidative carbonylation in a sulfone solvent, to increase the selectivity of the dialkyl succinate in the reaction products.

2. Process according to claim 1 wherein CO is introduced with a diluent as a mixture.

3. Process according to claim 1 wherein $O_2$ is introduced as air.

4. Process according to claim 1 wherein the sulfone is chosen from the group comprising structures (I), (II), or (III):

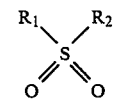

(I)

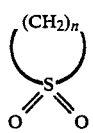

(II)

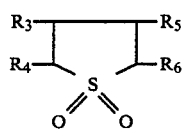

(III)

wherein $R_1$, $R_2$, $R_3$, $R_4$, $R_5$ and $R_6$ are independently selected from alkyl and cyclic hydrocarbon groups and $n \geq 4$.

5. Process according to claim 4 wherein the sulfone is sulfolane.

6. Process according to claim 4 wherein the sulfone has a higher boiling point than the dialkyl succinate.

7. Process according to claim 1 or 4 wherein the olefin contains 2-14 carbon atoms.

8. Process according to claim 7 wherein the olefin is ethylene.

9. Process according to claim 1 wherein the reaction temperature is from about 25° C. to about 250° C.

10. Process according to claim 1 wherein the reaction temperature is from 50° C. to 150° C.

11. Process according to claim 1 wherein the reaction pressure is from about 25 psig to about 2500 psig.

12. Process according to claim 1 wherein the reaction pressure is from 150 psig to 1500 psig.

13. Process according to claim 1 or 4 wherein the catalyst is a catalyst system comprising Pd metal or a Pd salt and an oxidant capable of oxidizing the Pd metal or salt to a Pd (II) state.

14. Process according to claim 13 wherein the Pd salt is a halide, nitrate, nitrite, acetate, or acetylacetonate.

15. Processs according to claim 13 wherein the oxidant is a salt or other compound containing copper, iron, molybdenum, chromium, manganese or vanadium.

16. Process according to claim 13 wherein the oxidant is an organic oxidant comprising a quinone or alkyl nitrite.

17. Process according to claim 15 wherein the salt or other compound is a halide, nitrite, nitrile, or carboxylate.

18. In the process for the oxidative carbonylation of ethylene to a dimethyl succinate with carbon monoxide, oxygen and an alcohol in the presence of a platinum group metal catalyst, the improvement which comprises the use of a sulfone solvent in the reaction step.

19. Process according to claim 18 wherein the catalyst is a catalyst system comprising Pd metal or a Pd salt and an oxidant capable of oxidizing the Pd metal or salt to a Pd (II) state.

20. Process according to claim 19 wherein the oxidant is a salt or other compound containing copper, iron, manganese, chromium, molybdenum or vanadium.

21. Process according to claim 19 wherein the oxidant is cuprous halide.

22. Process according to claim 18 or 19 wherein the sulfone is chosen from the group comprising structures (I), (II), or (III):

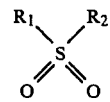

(I)

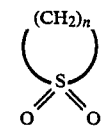

(II)

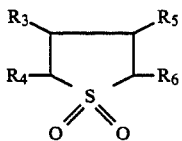

(III)

wherein $R_1$, $R_2$, $R_3$, $R_4$, $R_5$ and $R_6$ are alkyl or cyclic hydrocarbon groups which may be the same or different and $n \geq 4$.

23. Process according to claim 22 wherein the sulfone is sulfolane.

* * * * *